US012774999B2

(12) United States Patent
Fischer et al.

(10) Patent No.: US 12,774,999 B2
(45) Date of Patent: Oct. 27, 2026

(54) DEVICE FOR EXAMINING HATCHING EGGS

(71) Applicant: EVONTA-Technology GmbH, Dresden (DE)

(72) Inventors: Björn Fischer, Limbach-Oberfrohna (DE); Sven Meiner, Brand-Erbisdorf (DE)

(73) Assignee: EVONTA-TECHNOLOGY GMBH, Dresden (DE)

( * ) Notice: Subject to any disclaimer, the term of this patent is extended or adjusted under 35 U.S.C. 154(b) by 152 days.

(21) Appl. No.: 19/006,959

(22) Filed: Dec. 31, 2024

(65) Prior Publication Data

US 2025/0216370 A1 Jul. 3, 2025

(30) Foreign Application Priority Data

Jan. 3, 2024 (DE) ..................... 10 2024 000 143.3
Jan. 3, 2024 (DE) ..................... 20 2024 000 107.5

(51) Int. Cl.
*G01N 33/00* (2006.01)
*G01N 21/31* (2006.01)
(Continued)

(52) U.S. Cl.
CPC ............. *G01N 33/08* (2013.01); *G01N 21/31* (2013.01); *G01N 21/59* (2013.01); *G01N 2201/0438* (2013.01)

(58) Field of Classification Search
CPC ........ G01N 33/08; G01N 21/31; G01N 21/59; G01N 2201/0438
See application file for complete search history.

(56) References Cited

U.S. PATENT DOCUMENTS 2,987,182 A 6/1961 Ator et al.
2015/0308963 A1* 10/2015 Nambu .................. G01N 21/49 356/53

FOREIGN PATENT DOCUMENTS

CN 1742569 A 3/2006
DE 60003914 T2 5/2004
(Continued)

*Primary Examiner* — Kevin K Pyo
(74) *Attorney, Agent, or Firm* — HESLIN ROTHENBERG FARLEY & MESITI P.C.

(57) ABSTRACT

The invention relates to a device for examining hatching eggs with a transport device, light sources and cameras in connection with a data processing system. This is distinguished in particular by the fact that the presence of embryos in hatching eggs and their sex can be determined. For this purpose, the transport device has holders arranged next to one another for accommodating hatching eggs. The holders are located on belt drives. The holders have base plates with openings arranged in a row at a distance from one another for the placement of hatching eggs, walls arranged in a U-shape and tubular pieces so that the walls of adjacently arranged holders are tubular, and the tubular pieces and the walls are first light shafts. Light sources are located under holders, wherein they are arranged at a distance from hatching eggs in second light shafts. The cameras are arranged above holders so that, for the examination of hatching eggs, the first light shafts and the second light shafts form common light shafts, and hatching eggs are located between light sources and cameras. The cameras are connected to the data processing system.

20 Claims, 3 Drawing Sheets

(51) Int. Cl.
*G01N 21/59* (2006.01)
*G01N 33/08* (2006.01)

(56) References Cited

FOREIGN PATENT DOCUMENTS

| | | | |
|---|---|---|---|
| DE | 102007013107 | A1 | 9/2008 |
| DE | 102010006161 | B3 | 1/2011 |
| DE | 102007013107 | B4 | 2/2011 |
| DE | 102018001987 | A1 | 9/2019 |
| DE | 102019009002 | A1 | 6/2021 |
| EP | 2336751 | B1 | 9/2014 |

* cited by examiner

DEVICE FOR EXAMINING HATCHING EGGS

This application claims priority to German Patent Application No. 10 2024 000 143.3 and German Utility Patent No. 20 2024 000 107.5, both filed on Jan. 3, 2024. The entire contents of German Patent Application No. 10 2024 000 143.3 and German Utility Patent No. 20 2024 000 107.5 are hereby incorporated by reference herein.

The invention relates to a device for examining hatching eggs with a transport devices, light sources and cameras in connection with a data processing system.

Early assessment of hatching eggs in the hatching process is very important in particular for commercial poultry production. Of great interest is, inter alia, the developmental stage and determination of the sex of the hatching egg, taking animal welfare into account.

The publication DE 10 2007 013 107 A1 discloses a method for determining the sex of birds, wherein DNA-relevant cell material from the shaft of a young feather of the bird is examined. A spectrum arising from irradiation with light is compared with reference spectra so that a sex assignment of the bird can be made.

The publication DE 10 2010 006 161 B3 discloses a method and a device for determining the sex of fertilized and unincubated bird eggs, wherein an egg has a solid eggshell, an egg yolk surrounded by the eggshell and other egg shells, and a germinal disc associated with the egg yolk. To measure a spectrum, a probe is passed through a hole in the eggshell towards the germinal disc with germinal disc cells. The germinal disc cells are spectroscopically examined with the probe and the spectrum is classified. Considerable effort is required to determine the sex since the eggshell must be pierced.

The publication EP 2 336 751 B1 reveals a method for determining the sex of bird eggs, wherein electromagnetic radiation is emitted onto the germinal disc of an unincubated egg using a radiation source and, after switching off the radiation source, the decay behavior of the autofluorescence intensity excited by the electromagnetic radiation is recorded in a time- and spectrally resolved manner for at least one wavelength of the autofluorescence using a detector at the irradiated region of the germinal disc. From this, the respective egg is classified as female or male.

The publication DE 10 2019 009 002 A1 relates to a device for examining bird eggs, wherein at least one carrier with bird eggs arranged at a distance from one another is arranged between at least one source of electromagnetic waves and a color camera and/or a hyperspectral camera. The carrier has cutouts for placing the bird eggs. There are partitions between the bird eggs. Furthermore, the source of electromagnetic waves and the color camera and/or the hyperspectral camera are connected to a data processing system which determines characteristics from the image of the color camera and/or the transmission spectra recorded by the hyperspectral camera and assigns them to an embryo and therefore to the respective bird egg. With such an arrangement, scattered light in particular that influences the examination and therefore the identification of the respective bird egg and resulting incorrect identifications of the embryos cannot be ruled. Furthermore, sex-specific characteristics of embryos that are less developed in the earlier stage cannot be determined with certainty.

The publication DE 10 2018 001 987 A1 concerns a device for examining hatching eggs from the sixteenth day of incubation. For this purpose, a carrier with hatching eggs arranged at a distance from each other is arranged between a source of electromagnetic waves and a hyperspectral camera. The carrier also has cutouts for placing the hatching eggs and a light-tight coupling of the electromagnetic waves. There are partitions between the hatching eggs. The source of electromagnetic waves and the hyperspectral camera are connected to a data processing system which determines the egg images from the image of the hyperspectral camera and assigns hyperspectral data and the position of the respective hatching egg on the carrier to the respective egg image.

The publication DE 600 03 914 T2 includes a method and a device for the selective classification of chicken eggs, wherein clear eggs are identified from a plurality of eggs using the egg opacities. A spatial temperature trend is determined from the plurality of eggs using the identification of clear eggs. From this, live eggs are identified from the plurality of eggs using the spatial temperature trend. The device has a light-transillumination system to determine egg opacity. Furthermore, the device for examining egg temperatures possesses a thermal transillumination system which detects the egg temperatures and generates temperature signals that correspond to the egg temperatures. For this purpose, an infrared emitter and an infrared detector are used as the light transillumination system and an infrared sensor is used as the thermal transillumination system.

The publication U.S. Pat. No. 2,987,182 A relates to a device for examining the presence or the absence of blood in eggs. For this purpose, the device has a conveyor for eggs and a trough for placing and examining an egg using a light source and photoelectric detectors.

The publication CN 1 742 569 A discloses a method and a device for determining the sex of domestic chickens in the early incubation phase of embryo eggs. The device has in particular a digital camera and a light source. The creation of a bloodline diagram of an incubated embryonic egg forms the basis.

The invention specified in patent claim 1 is based on the object of determining the presence of embryos in hatching eggs and their sex.

This object is achieved by means of the features listed in claim 1.

The device for examining hatching eggs with a transport device, light sources and cameras in conjunction with a data processing system is distinguished in particular by the fact that the presence of embryos in hatching eggs and their sex can be determined.

For this purpose, the transport device has holders arranged next to one another for accommodating hatching eggs. The holders are located on two belt drives arranged parallel at a distance from each other. The holders have base plates with openings arranged in a row at a distance from one another for the placement of hatching eggs, U-shaped walls and tubular pieces, so that the openings and the tubular pieces of the holders are located between the belt drives, the walls of adjacently arranged holders are tubular, and the tubular pieces and the walls are first light shafts for the placement of hatching eggs and when placing hatching eggs. Light sources arranged in a matrix or matrices are located under holders, wherein the light sources are arranged at a distance from hatching eggs in second light shafts for exposing hatching eggs of several holders to electromagnetic waves. The cameras are arranged above holders so that, for the examination of hatching eggs, the first light shafts and the second light shafts form common light shafts, and hatching eggs from rows or from regions of rows are located between light sources and cameras. The cameras are connected to the data processing system for detecting empty spaces and the states of hatching eggs.

The holders, sequentially in a row, advantageously form the first light shafts for placing one hatching egg in each light shaft, and therefore the first light shafts with one hatching egg each. The tubular pieces connected to the openings in the base plates are the first components of the first light shafts. The legs of the U-shaped walls are side walls on the base plates or the tubular pieces and represent the second components of the first light shafts. Furthermore, the middle parts of the U-shaped walls of a holder are each both rear walls of the second components of first light shafts as well as front walls of the second components of the first light shafts of the downstream holder. When positioning first light shafts with hatching eggs corresponding to the second light shafts with the light sources, continuous light shafts are formed, each with one hatching egg and one light source. This means that a light source can be assigned to each hatching egg to be examined. At the same time, scattered light is largely avoided when examining hatching eggs so that an improved examination and therefore reliable identification of the respective hatching egg is possible using the cameras.

The cross-sections of the openings and the tubular pieces are in particular circles. The diameter of the openings in this case can be smaller than or equal to the diameter of the tubular pieces. The openings and/or tubular pieces are also advantageously simultaneously holders for the hatching eggs. For this purpose, the diameters of the openings and/or the tubular pieces are smaller than the largest cross-sections of the hatching eggs. The length of the tubular pieces is so large that placed hatching eggs do not protrude beyond the holders.

The end regions of the legs of the U-shaped walls of the holders can be further angled. At the same time, the middle parts of the U-shaped walls in the direction of subsequent holders can possess wall sections which partially overlap the angled end regions of the legs of the U-shaped walls of the subsequent holder. This reduces gaps between the first light shafts of the holders arranged one after the other as much as possible during the examination of the hatching eggs.

The holders are located in this case on belt drives arranged parallel at a distance from each other so that a continuous conveyor belt is formed with the holders. At the same time, space-saving deflections are available. The second light shafts with the light sources are located between the deflections and the continuous conveyor belt.

Advantageous embodiments of the invention are set out in the following developments and embodiments. These can equip the device for examining hatching eggs with a transport device, light sources and cameras in conjunction with a data processing system, individually or in combination.

In one embodiment, between light shafts arranged corresponding to one another, there is at least one thermally stable glass pane or glass ceramic pane with optical transmittivity adapted to the light sources. This provides protection of the light sources in particular from damaged hatching eggs. At the same time, the individual holders and the glass pane are easy to clean.

In one embodiment, the light sources arranged in a matrix are an assembly with recesses for accommodating the light sources. Furthermore, the assembly has at least one cooling device. This can be a passive and/or an active heat sink. In addition, the assembly can have at least one cooling channel with connections for a flowable medium. The assembly can also consist of interconnected components so that a continuous cooling channel for the recesses with the light sources can be easily realized.

In one embodiment, at least one first and one second assembly with light sources and at least one first and at least one second camera are arranged under holders in the transport direction of the hatching eggs. The first assembly and the first camera serve to determine empty spaces and hatching eggs with increased or reduced intensity/transmittivity. The latter occurs in particular when there are heavily contaminated, germ-contaminated or overdeveloped hatching eggs. The second assembly and the second camera are advantageously used to determine different optical properties of the sexes of the embryos.

For example, the cameras can be color cameras, hyperspectral area cameras and/or hyperspectral line cameras. Conveniently, a color camera can be used for the first group and at least one hyperspectral camera for the second group. Groups of line scan cameras can also be used.

In one embodiment, the data processing system is designed so that, during the examination:

increased intensity/transmittivity, reduced intensity/transmittivity, the presence of at least one pigment of a female embryo or the presence of at least one sex-specific optical characteristic of at least one of the two sexes is determined and assigned to the respective position of the hatching egg in the holder.

Increased intensity/transmittivity occurs especially in an unfertilized egg, underdeveloped embryos or voids. A reduced intensity/transmittivity can be attributed in particular to an infected hatching egg, an overdeveloped hatching egg or a dirty hatching egg. These hatching eggs are removed and not incubated further.

In one embodiment, the light sources are interconnected with the data processing system in such a way that the light sources can be switched on, switched off, and their light outputs can be adjusted according to the findings of the hatching eggs. The latter is achieved in particular by dimming. Light sources with a wavelength ranging from 400 nm to 1000 nm can be used as light sources of at least the second assembly. These can be halogen lamps or light-emitting diodes in particular.

In one embodiment, a diaphragm with circular cutouts arranged corresponding to the light sources is located on the thermally stable glass pane or glass-ceramic pane.

In one embodiment, the device for examining hatching eggs is associated with a device for supplying hatching eggs to be examined to the holders and/or at least one device for removing hatching eggs from holders. The device supplying hatching eggs and/or the device removing hatching eggs each has or have a carrier with holding elements arranged in matrices. Furthermore, the carrier is connected to a linear drive and a lifting device.

In one embodiment, holding elements of the carrier are driven together and guided so that the distance of the holding elements to each other increases or decreases. In continuation, the guides of a row can be designed to be straight or fan-shaped, running transversely to the transport direction of the hatching eggs.

An embodiment of the invention is shown in principle in each of the drawings and is described in more detail below.

A device for examining hatching eggs substantially consists of a transport device 1, light sources 2 and cameras 3 in conjunction with a data processing system 4.

Figure 1:
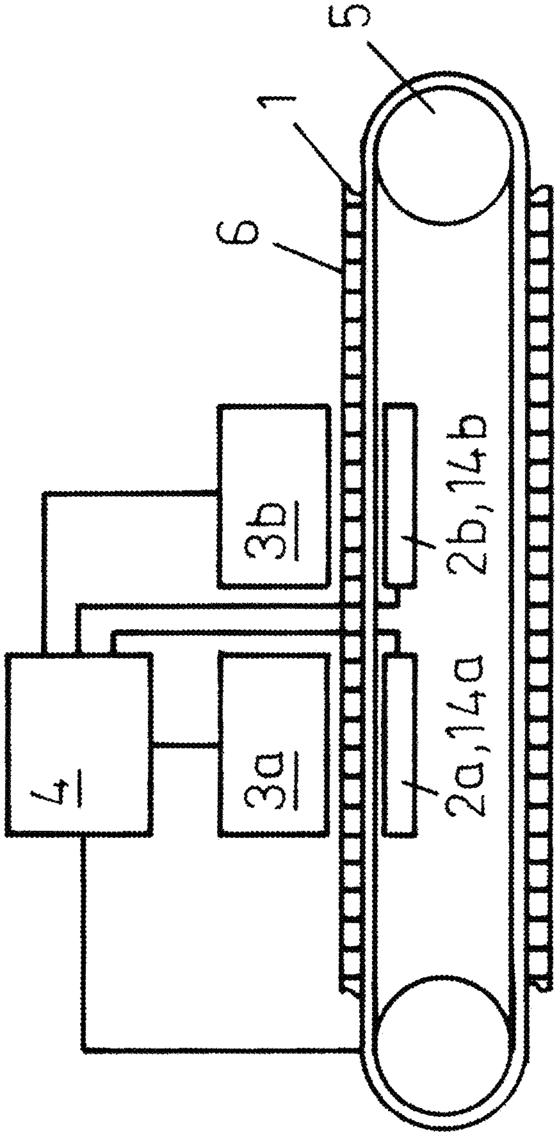
FIG. 1 shows a device for examining hatching eggs.

FIG. 1 shows the basic representation of a device for examining hatching eggs.

The transport device 1 possesses holders 6 arranged next to one another for accommodating hatching eggs 7. The holders 6 are located on two belt drives 5 arranged parallel to each other and therefore form a continuous conveyor belt. At least one of the belt drives 5 is connected to a drive which is further connected to the data processing system 4. The cameras 3 are arranged above the transport device 1. For this purpose, at least one first camera 3*a* and at least one second camera 3*a* are arranged one after the other in the transport direction of the hatching eggs 7. The light sources 2 are located between the continuous conveyor belt formed by the belt drives 5 in connection with the holders 6 as well as their deflections. First light sources 2*a* and second light sources 2*b* are arranged one after the other in the transport direction of the hatching eggs 7.

Figure 2:
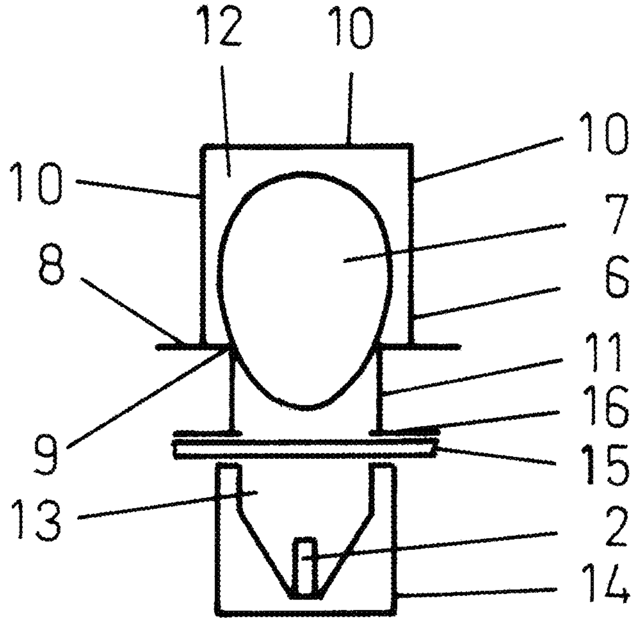
FIG. 2 shows a section of a holder in connection with a light source for examining a hatching egg in a side view.

FIG. 2 shows a section of a holder 6 in connection with a light source 2 for examining a hatching egg 7 in a basic side view.

The holders 6 possess base plates 8 with openings 9 arranged in a row at a distance from one another for the placement of hatching eggs 7, walls 10 arranged in a U-shape, and tubular pieces 11. The openings 9 and the tubular pieces 11 of the holders 6 are located between the belt drives 5. The walls 10 of adjacently arranged holders 6 are tubular. The walls 10 and the tubular pieces 11 are first light shafts 12 for the placement of hatching eggs 7 and when placing hatching eggs 7. Light sources 2*a*, 2*b* arranged in a matrix or matrices are located under holders 6, wherein the light sources 2*a*, 2*b* are arranged at a distance from hatching eggs 7 in second light shafts 13 for exposing hatching eggs 7 of several holders 6 to electromagnetic waves. The light sources 2*a*, 2*b* arranged in a matrix are each an assembly 14 with recesses 13 for accommodating the light sources 2*a*, 2*b*. The recesses 13 are simultaneously the second light shafts 13. The assembly 14 can possess at least one cooling channel with connections for a flowable medium. Between light shafts 12, 13 arranged corresponding to one another, there can be at least one thermally stable glass pane 15 or glass ceramic pane with optical transmitivity adapted to the light sources 2. Furthermore, a diaphragm 16 with circular cutouts arranged corresponding to the light sources 2 can be located on the thermally stable glass pane 15 or glass ceramic pane.

The cameras 3*a*, 3*b* are arranged above holders 6 so that, for the examination of hatching eggs 7, the first light shafts 12 and the second light shafts 13 form common light shafts, and hatching eggs 7 from rows or from regions of rows are located between light sources 2 and cameras 3*a*, 3*b*. The cameras 3*a*, 3*b* are connected to the data processing system 4 for detecting empty spaces and the states of hatching eggs 7.

Figure 3:
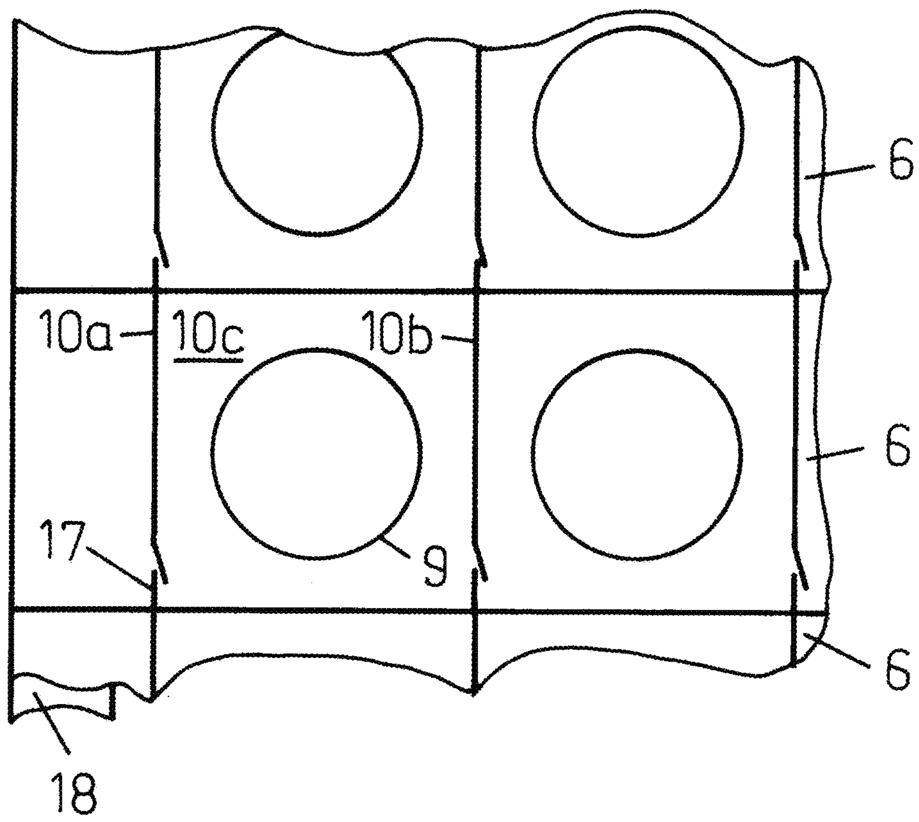
FIG. 3 shows a section of a holder in a plan view.

FIG. 3 shows a section of a holder 6 in a basic plan view.

The holders 6 possess the walls 10 arranged in a U-shape. The end regions of the legs 10*a*, 10*b* of the U-shaped walls 10 of the holders 6 can be angled. At the same time, the middle parts 10*c* of the U-shaped walls 10 in the direction of subsequent holders 6 can possess wall sections 17 which partially overlap the angled end regions of the legs 10*a*, 10*b* of the U-shaped walls 10 of the subsequent holder 6. This minimizes gaps between the first light shafts 12 of the holders 6 arranged one after the other during the examination of the hatching eggs 7. The holders 6 are attached to the belt drives 5. Toothed belts 18 can be used as belts 18.

In the transport direction of the hatching eggs 7, at least one first assembly 14*a* with light sources 2*a* and a second assembly 14*b* with light sources 2*b* and at least one first camera 3*a* and at least one second camera 3*b* are arranged under holders 6. The first assembly 14*a* and the first camera 3*a* serve to determine empty spaces and hatching eggs with increased intensity/transmittivity. The second assembly 14*b* and the second camera 3*b* serve to determine the sex of the embryos. The cameras 3*a*, 3*b* can be area cameras 3*a*, 3*b* and/or line cameras 3*a*, 3*b* and/or an area camera 3*a* and at least one line camera 3*b*. Color cameras 3*a*, 3*b* and/or hyperspectral cameras 3*a*, 3*b* can be used for this purpose.

The light sources 2 can advantageously possess wavelengths ranging from 400 nm to 1000 nm. These can be halogen lamps or light-emitting diodes.

The data processing system 4 is designed so that, during the examination:

- increased intensity/transmittivity, for example in the case of an unfertilized egg 7, underdeveloped embryos or empty spaces,
- reduced intensity/transmittivity, for example in the case of an infected hatching egg 7, an overdeveloped hatching egg 7, a contaminated hatching egg 7,
- the presence of at least one pigment in a female embryo, or
- the presence of at least one sex-specific characteristic in a female embryo is determined and assigned to the respective position of the hatching egg 7 in the holder 6.

The light sources 2 can be interconnected with the data processing system 4 in such a way that the light sources 2 can be switched on, switched off, and their light outputs can be adjusted according to the findings of the hatching eggs 7. Light sources 2 are accordingly dimmable.

In one embodiment, the device for examining hatching eggs 7 can be associated with a device for supplying hatching eggs 7 to be examined to the holders 6 and/or at least one device for removing hatching eggs 7 from holders 6. For this purpose, the device supplying the hatching eggs 7 and/or the device removing the hatching eggs 7 can each have a carrier with holding elements arranged in matrices. The carrier can also be connected to a linear drive and a lifting device. Holding elements can be, for example, suction cups. The holding elements of the carrier can be driven and together moveably guided so that the distance of the holding elements to each other increases or decreases. For this purpose, the guides of a row can be designed to be straight or fan-shaped, running transversely to the transport direction of the hatching eggs.

The invention claimed is:

1. A device for examining hatching eggs (7) in connection with a data processing system (4), said device for examining hatching eggs comprising a transport device (1), light sources (2) and cameras (3), wherein the transport device (1) has holders (6) arranged next to one another for accommodating hatching eggs (7), the holders (6) are located on two belt drives (5) arranged at a distance parallel to one another, the holders (6) have base plates (8) with openings (9) arranged in a row at a distance from one another for placing hatching eggs (7), walls (10) arranged in a U-shape and tubular pieces 11 so that the openings (9) and the tubular pieces (11) of the holders (6) are located between the belt drives (5), the walls (10) of adjacently arranged holders (6) are tubular, and the walls (10) and the tubular pieces (11) are first light shafts (12) for placing hatching eggs (7) and when placing with hatching eggs (7), light sources (2) arranged in a matrix or in matrices are located under holders (6), wherein the light sources (2) are arranged at a distance from hatching eggs (7) in second light shafts (13) for exposing hatching eggs (7) in several holders (6) to electromagnetic waves, the cameras (3) are arranged above holders (6) so that the first light shafts (12) and the second light shafts (13) form common light shafts for examining hatching eggs (7), and hatching eggs (7) from rows or from regions of rows are located between light sources (2) and cameras (3), and the cameras (3) are connected to the data processing system (4) for detecting empty spaces and the states of hatching eggs (7).

2. The device according to claim 1, wherein between light shafts arranged corresponding to one another, there is at least one thermally stable glass pane (15) or glass ceramic pane with optical transmittivity adapted to the light sources (2).

3. The device according to claim 1, wherein the light sources (2) arranged in a matrix are an assembly (14) with recesses for accommodating the light sources (2), and the assembly (14) possesses at least one cooling device.

4. The device according claim 1, wherein, in the transport direction of the hatching eggs (7), at least one first assembly (14*a*) and one second assembly (14*b*) with light sources (2) and at least one first camera (3*a*) and at least one second camera (3*b*) are arranged under holders 6, wherein the first assembly (14*a*) and the first camera (3*a*) serve to determine empty spaces and hatching eggs (7) with increased or reduced intensity/transmittivity, and wherein the second assembly (14*b*) and the second camera (3*b*) serve to determine different optical properties of the sexes of the embryos.

5. The device according to claim 1, wherein the data processing system (4) is designed such that during the examination:

increased intensity/transmittivity,
reduced intensity/transmittivity,
the presence of at least one pigment in a female embryo, or
the presence of at least one sex-specific optical characteristic of at least one of the two sexes
is determined and assigned to the respective position of the hatching egg (7) in the holder (6).

6. The device according to claim 1, wherein the light sources (2) are connected to the data processing system (4) in such a way that the light sources (2) can be switched on, switched off, and their light outputs can be adjusted according to the findings of the hatching eggs (7).

7. The device according to claim 1, wherein a diaphragm (16) with circular cutouts arranged corresponding to the light sources (2) is located on the thermally stable glass pane (15) or glass ceramic pane.

8. The device according to claim 1, wherein the device for examining hatching eggs (7) is assigned a device supplying hatching eggs (7) to be examined to the holders (6) and/or at least one device for removing hatching eggs (7) from holders (6), wherein the device supplying the hatching eggs (7) and/or the device removing the hatching eggs (7) each has or have a carrier with holding elements arranged in matrices, and wherein the carrier is connected to a linear drive and a lifting device.

9. The device according to claim 1, wherein holding elements of the carrier are driven together and moveably guided so that the distance of the holding elements to each other increases or decreases.

10. The device according to claim 1, wherein the guides of a row are designed to run straight and fan-shaped transversely to the transport direction of the hatching eggs (7).

11. The device according to claim 2, wherein the light sources (2) arranged in a matrix are an assembly (14) with recesses for accommodating the light sources (2), and the assembly (14) possesses at least one cooling device.

12. The device according claim 11, wherein, in the transport direction of the hatching eggs (7), at least one first assembly (14*a*) and one second assembly (14*b*) with light sources (2) and at least one first camera (3*a*) and at least one second camera (3*b*) are arranged under holders 6, wherein the first assembly (14*a*) and the first camera (3*a*) serve to determine empty spaces and hatching eggs (7) with increased or reduced intensity/transmittivity, and wherein the second assembly (14*b*) and the second camera (3*b*) serve to determine different optical properties of the sexes of the embryos.

13. The device according to claim 12, wherein the data processing system (4) is designed such that during the examination:

increased intensity/transmittivity,
reduced intensity/transmittivity,
the presence of at least one pigment in a female embryo, or
the presence of at least one sex-specific optical characteristic of at least one of the two sexes
is determined and assigned to the respective position of the hatching egg (7) in the holder (6).

14. The device according to claim 13, wherein the light sources (2) are connected to the data processing system (4) in such a way that the light sources (2) can be switched on, switched off, and their light outputs can be adjusted according to the findings of the hatching eggs (7).

15. The device according to claim 14, wherein a diaphragm (16) with circular cutouts arranged corresponding to the light sources (2) is located on the thermally stable glass pane (15) or glass ceramic pane.

16. The device according to claim 15, wherein the device for examining hatching eggs (7) is assigned a device supplying hatching eggs (7) to be examined to the holders (6) and/or at least one device for removing hatching eggs (7) from holders (6), wherein the device supplying the hatching eggs (7) and/or the device removing the hatching eggs (7) each has or have a carrier with holding elements arranged in matrices, and wherein the carrier is connected to a linear drive and a lifting device.

17. The device according to claim 16, wherein holding elements of the carrier are driven together and moveably guided so that the distance of the holding elements to each other increases or decreases.

18. The device according to claim 17, wherein the guides of a row are designed to run straight and fan-shaped transversely to the transport direction of the hatching eggs (7).

19. The device according claim 2, wherein, in the transport direction of the hatching eggs (7), at least one first assembly (14*a*) and one second assembly (14*b*) with light sources (2) and at least one first camera (3*a*) and at least one second camera (3*b*) are arranged under holders 6, wherein the first assembly (14*a*) and the first camera (3*a*) serve to determine empty spaces and hatching eggs (7) with increased or reduced intensity/transmittivity, and wherein the second assembly (14*b*) and the second camera (3*b*) serve to determine different optical properties of the sexes of the embryos.

20. A method for determining the presence of an embryo in an egg, and/or for determining the sex of an embryo in an egg, said method comprising processing the egg through the device for examining hatching eggs according to claim 1.

* * * * *